United States Patent [19]

King

[11] Patent Number: 5,089,626

[45] Date of Patent: Feb. 18, 1992

[54] PROCESS FOR PREPARING AN ANGIOTENSIN II ANTAGONIST

[75] Inventor: Anthony O. King, Hillsborough, N.J.

[73] Assignee: Merck & Co., Inc., Rahway, N.J.

[21] Appl. No.: 571,398

[22] Filed: Aug. 23, 1990

[51] Int. Cl.$^5$ .......................................... C07D 401/10
[52] U.S. Cl. ................................................ 548/253
[58] Field of Search ....................................... 548/253

[56] References Cited

FOREIGN PATENT DOCUMENTS 0253310 1/1988 European Pat. Off. .

OTHER PUBLICATIONS

March, Jerry, Advanced Organic Chemistry Reactions, Mechanisms, and Structure, Third Ed., New York, pp. 1057-1060 (1985).

Streitwieser, A. Jr. et al., Introduction to Organic Chemistry, Third Ed., New York, pp. 365-366 (1985).

*Primary Examiner*—Mary C. Lee
*Assistant Examiner*—Lenora Mittenberger
*Attorney, Agent, or Firm*—William H. Nicholson; Joseph F. DiPrima

[57] ABSTRACT

There is disclosed a process for preparing the active metabolite of an angiotensin II antagonist from its pro-drug compound.

20 Claims, No Drawings

PROCESS FOR PREPARING AN ANGIOTENSIN II ANTAGONIST

BACKGROUND OF THE INVENTION

This invention relates to a process for preparing the active metabolite of an angiotensin II antagonist from its pro-drug compound. The active metabolite obtained can then be administered as an antihypertensive agent to a person in need of such treatment.

Administration of the active metabolite as opposed to its pro-drug analog is beneficial to a person receiving such treatment as the metabolite does not have to undergo any further, biochemical (i.e., metabolic) change by the body, but is available to be delivered by the body to its site of action. In addition, the active metabolite is about twenty times more potent than its pro-drug analog so that less metabolite is needed to achieve the same therapeutic effect as its pro-drug.

Administration of the pro-drug analog, on the other hand, requires the body to biochemically transform (i.e., metabolize) the pro-drug analog to its active, metabolic form. Usually, this biochemical transformation occurs in the renal system (generally, the kidney) causing the body to work harder and raising the possibility of creating adverse side effects.

The pro-drug analog compound used in the process of this invention is a substituted imidazole as disclosed in European Patent Application 253,310, published Jan. 20, 1988, which is included herein by reference. This European Application also discloses a two-step process for obtaining an active substituted imidazole metabolite from its pro-drug analog. This two-step process requires two oxidation reactions to obtain the desired, active metabolite. However, the metabolite obtained from this two-step process is difficult to purify and results in low yields of the desired metabolite.

SUMMARY OF THE INVENTION

It has now been found that the active metabolite of a substituted imidazole angiotensin II antagonist pro-drug compound can be readily and economically obtained from the direct, one-step oxidation process of this invention. By employing the process of this invention, fewer reactions and reagents are required and the desired, active, substituted imidazole metabolite compound is obtained in higher yield and greater purity.

In general, the process of the invention comprises, reacting a compound having the formula:

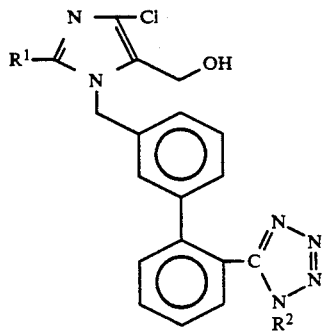

wherein $R^1$ is $C_1-C_{10}$-alkyl and $R^2$ is H, K, Na or Li, in the presence of an aqueous base and an oxidizing agent to obtain a compound having the formula:

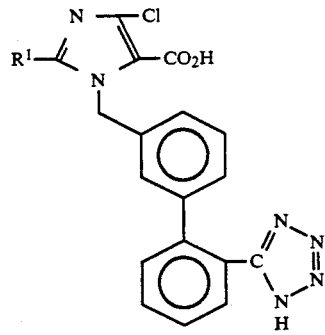

wherein $R^1$ is as defined above, followed by isolation and purification of the formula I compound. The formula II compound is the substituted imidazole pro-drug of the active, metabolite formula I compound.

The bases that can be used in the process of this invention are members selected from the group consisting of NaOH, LiOH, KOH, and the like.

Although such bases as $K_2HPO_4$ and $Na_2CO_3$ can also be used in this process, they result in lower yields of the desired formula I compound which then contains more impurities making it more difficult, time consuming and costly to produce the desired product. When the preferred bases are employed in the process of the invention, the formula I compound is obtained in significantly higher yields of greater than about 80% and substantially higher purity of about 98% after purification.

The concentration of aqueous base employed should be from about 0.1M to about 5.0M; i.e., from about 10 mL to about 50 mL, preferably about 20 mL, for each gram of formula II compound used.

In one embodiment of the invention, a strong oxidizing agent such as $KMnO_4$ is employed. When such an oxidizing agent is used, the reaction proceeds rapidly to completion without the need for additional reagents such as catalysts.

In another embodiment of the invention, relatively weaker oxidizing agents can be employed such as $K_2S_2O_8$, NaOCl, NaOBr, $NaIO_4$, $KIO_4$, and the like. When these relatively weaker oxidizing agents are used, a ruthenuim metal catalyst is also added to the reaction mixture to speed up the rate of reaction and assure that the reaction goes to completion. In this embodiment, the ruthenuim metal catalyst employed is a member of the group consisting of $RuX_3$ where X is Cl, Br or I; hydrated $RuX_3$ where X is as defined above; $RuO_2$; hydrated $RuO_2$; $RuO_4$; Ru metal powder; Ru on carbon (i.e. Ru/C); Ru (III) acetylacetone; Ru on alumina (i.e., $Ru/Al_2O_3$); and the like.

In both embodiments of the process of the invention, the oxidizing agent should be present in an amount of about 2.0 mole equivalents for each mole of formula II compound; the catalyst should be present in an amount of from about 0.1 mol % to about 20 mol %, preferably about 5 mol %; the temperature of the reaction mixture can be from about $-20°$ C. to about $50°$ C., preferably from about $0°$ C. to about $25°$ C.; and, the pH of the reaction mixture should be greater then pH 12, preferably from about pH 13 to about pH 14.

Generally, isolation of the formula I compound from the reaction mixture and removing impurities from it can be accomplished by employing HCl gas and isopropylacetate (iPAc) to isolate the crude formula I compound and liberate it as a free base; chromatographing the isolated formula I compound to remove polar impurities therefrom; reforming the formula I compound by treating it with HCl and iPAc; and, recrystallizing the reformed formula I compound using iPAc/CH$_3$OH to remove the less polar impurities. Alternatively, the isolated formula I compound free base can first be chromatographed followed by reformation and recrystallization.

While the process of the invention can be employed to obtain active metabolite formula I compounds in the full range of $R^1$, the preferred metabolite is where $R^1$ is $C_4H_9$.

DETAILED DESCRIPTION OF THE INVENTION

The following examples are set forth to further illustrate the process of the invention and, as such, they are not intended nor should they be construed as limiting the invention set forth in the appended claims.

EXAMPLE 1

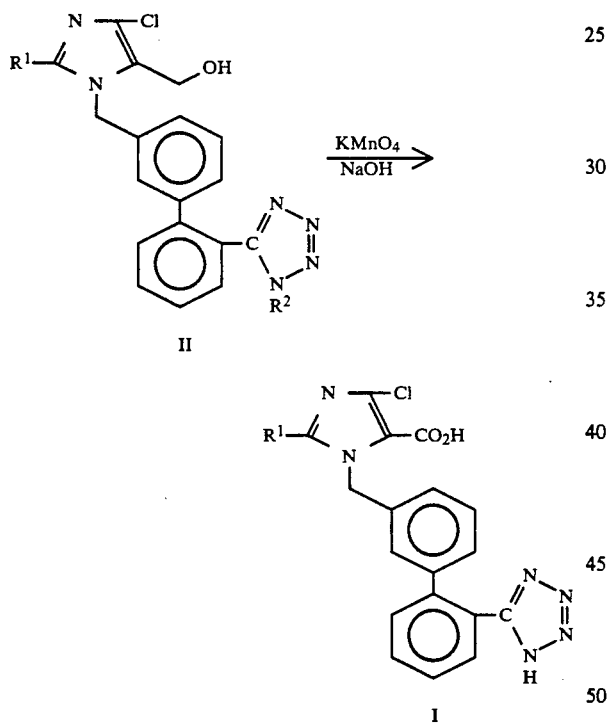

A five (5) liter round bottom flask fitted with an overhead stirred was charged with 4 L of 0.25N sodium hydroxide and 200 g of formula II compound. The homogeneous reaction mixture was stirred in a room temperature water bath as 141.8 g of potassium permanganate (KMnO$_4$) were added over a two hour period while maintaining the temperature of the reaction mixture below 25° C. The reaction was monitored by high pressure liquid chromatography (HPLC) to completion.

The aqueous reaction mixture was filtered through a fine diatomaceous earth filter-aid and acidified to pH 4 with 80 mL of concentrated HCl. The aqueous phase was extracted with 2×1000 mL of ethyl acetate and the combined layers were dried with 30 g of magnesium sulfate. The ethyl acetate was displaced with isopropyl acetate (iPAc), and the final volume was adjusted to 18 liters with iPAc.

The iPAc solution was charged into a 22 liter round-bottomed flask fitted with an overhead stirrer and dry HCl gas was passed into the solution which resulted in a white precipitate salt. The salt was collected by filtration and added to a separatory funnel containing 2 L of ethyl acetate (EtOAc) and 2 L of water. The aqueous phase pH was adjusted to 4 with 5N NaOH and the layers were separated. The EtOAc layer was dried over magnesium sulfate, evaporated in vacuo to a foam, and the foam dissolved in a minimal amount of methylene chloride/ethyl acetate/acetic acid (90/10/3).

A silica gel (SiO$_2$) chromatograph column (1500 g) was prepared in methylene chloride/ethyl acetate/acetic acid (90/10/3), the product was loaded on, and the column eluted with methylene chloride/ethyl acetate/acetic acid (90/10/3). Fractions were checked by HPLC and the combined fractions (20 L) were concentrated to dryness. The resulting foam was dissolved in iPAc and the final volume was adjusted to 12 L with iPAc.

The iPAc solution was then charged into a 22 liter round-bottomed flask and anhydrous HCl was passed into the solution. The resulting white precipitate was collected by filtration and the wet solid was added to a flask fitted with an overhead stirrer containing 1.6 L of hot methanol (MeOH) and, with stirring, the solution became homogeneous. To this there was then added 3.2 L of iPAc and the solution was cooled to −15° C. The salt began to precipitate upon cooling and the remainder was precipitated by the slow addition of 3.2 L of iPAc. The resultant solid was filtered and washed with iPAc and dried under a high vacuum at 40° C. overnight. The yield was 70 g (>99 wt % pure) of the formula I compound as the hydrochloride salt.

EXAMPLE 2

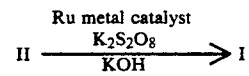

To a mixture of formula II compound (2.0 g) and RuCl$_3$.3H$_2$O (0.06 g) in 1M of aqueous KOH (40 ml) at 0° C. there was added K$_2$S$_2$O$_8$ (2.4 g). The reaction mixture was aged at 0° C. to 5° C. for 12 hours at which time the reaction was completed. Methanol (MeOH) (0.5 ml) was then added and the reaction mixture was allowed to warm to room temperature over 30 minutes. The mixture was then filtered through a pad of diatomaceous earth filter-aid to remove precipitated Ru catalyst and the pad was rinsed with water (10 ml). The filtrate was cooled to 0° C. and acidified with 6N aqueous HCl to pH 4. Upon acidification, formula I compound crystallized out of the water solvent and was filtered. The product was air dried on the filter and then further dried in vacuo at 50° C. The yield was 2.0 g (98.5 wt % pure) of the formula I compound.

What is claimed is:

1. A process for preparing a compound having the formula:

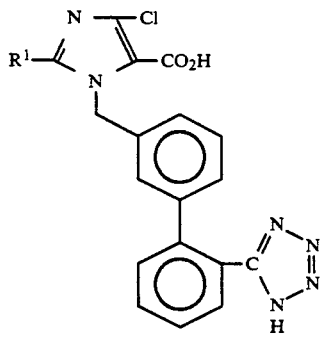

wherein $R^1$ is $C_1$–$C_{10}$-alkyl, which process comprises:
(a) reacting a compound having the formula:

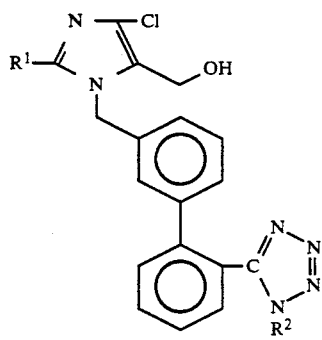

wherein $R^1$ is as defined above and $R^2$ is H, K, Na or Li, in an aqueous base reaction mixture in the presence of an oxidizing agent and a ruthenium metal catalyst said oxidizing agent being a member selected from the group consisting of $K_2S_2O_8$, NaOCl, NaOBr, $NaIO_4$ and $KIO_4$;
(b) isolating said formula I compound from said reaction mixture and,
(c) removing impurities from said formula I compound.

2. The process of claim 1 wherein said base is a member of the group consisting of NaOH LiOH and KOH and is present in an amount of from about 10 mL to about 50 mL.

3. The process of claim 2 wherein said base is present in an amount of about 20 mL.

4. The process of claim 1 wherein said oxidizing agent is present in an amount of about 2.0 mole equivalents per each mole of said formula II compound.

5. The process of claim 1 wherein said ruthenium metal catalyst is a member selected from the group consisting of $RuX_3$ where X is Cl, Br or I, hydrated $RuX_3$ where X is as defined above, $RuO_2$, hydrated $RuO_2$, $RuO_4$, Ru metal powder, Ru/C, Ru (III) acetylacetone, and $Ru/Al_2O_3$.

6. The process of claim 5 wherein said catalyst is present in an amount of from about 0.1 mol % to about 20 mol %.

7. The process of claim 6 wherein said catalyst is present in an amount of about 5 mol %.

8. The process of claim 1 wherein the temperature of said reaction mixture is from about $-20°$ C. to about $50°$ C.

9. The process of claim 8 wherein said temperature is from about $0°$ C. to about $25°$ C.

10. The process of claim 1 wherein the pH is said reaction mixture is greater than about pH 12.

11. The process of claim 10 wherein said pH is from about 13 to about pH 14.

12. The process of claim 1 wherein $R^1$ is $C_4H_9$.

13. A process for preparing a compound having the formula:

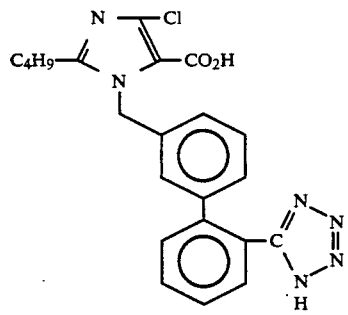

which process comprises:
(a) reacting a compound having the formula:

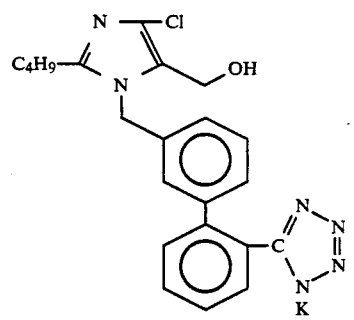

in an aqueous base reaction mixture at a pH of greater than about pH 12 and a temperature of from about $-20°$ C. to about $50°$ C. in the presence of an oxidizing agent and a ruthenium metal catalyst said base being a member selected from the group consisting of NaOH, LiOH and KOH; said oxidizing agent being a member selected from the group consisting of $K_2S_2O_8$, NaOCl, NaOBr, $NaIO_4$ and $KIO_4$; said catalyst being a member selected from the group consisting of $RuX_3$ where X is CL Br or I, hydrated $RuX_3$, where X is defined above, $RuO_2$, hydrated $RuO_2$, $RuO_4$, Ru metal powder, Ru/C, Ru(II) acetylacetone, and $Ru/Al_2O_3$;
(b) isolating said formula I compound from said reaction mixture and,
(c) removing impurities from said formula I compound.

14. The process of claim 13 wherein said base is present in an amount of from about 10 mL to about 50 mL.

15. The process of claim 14 wherein said base is present in an amount of about 20 mL.

16. The process of claim 13 wherein said oxidizing agent is present in an amount of about 2.0 mole equivalents per each mole of said formula II compound.

17. The process of claim 13 wherein said catalyst is present in an amount of from about 0.1 mol % to about 20 mol %.

18. The process of claim 17 wherein said catalyst is present in an amount of about 5 mol %.

19. The process of claim 13 wherein said temperature is from about $0°$ C. to about $25°$ C.

20. The process of claim 13 wherein the pH of said reaction mixture is from about pH 13 to about pH 14.

* * * * *